United States Patent
Sambongi

(10) Patent No.: US 8,700,355 B2
(45) Date of Patent: Apr. 15, 2014

(54) POSITIONING APPARATUS JUDGING MOVING METHOD TO CONTROL POSITIONING TIMING

(75) Inventor: Masao Sambongi, Hachioji (JP)

(73) Assignee: Casio Computer Co., Ltd., Tokyo (JP)

( * ) Notice: Subject to any disclaimer, the term of this patent is extended or adjusted under 35 U.S.C. 154(b) by 420 days.

(21) Appl. No.: 13/224,044

(22) Filed: Sep. 1, 2011

(65) Prior Publication Data
US 2012/0059623 A1  Mar. 8, 2012

(30) Foreign Application Priority Data

Sep. 2, 2010 (JP) ................................. 2010-196304

(51) Int. Cl.
*G06F 19/00* (2011.01)
*G03F 7/20* (2006.01)
*A61B 18/20* (2006.01)

(52) U.S. Cl.
CPC ........... *G03F 7/70775* (2013.01); *A61B 18/203* (2013.01)
USPC ........................................................ 702/150

(58) Field of Classification Search
CPC .............. G03F 7/70775; A61B 18/203; A61B 2017/00154; A61B 2017/00769; A61B 2018/00458
See application file for complete search history.

(56) References Cited

U.S. PATENT DOCUMENTS

2003/0217070 A1  11/2003  Gotoh et al.
2008/0252527 A1*  10/2008  Garcia ......................... 342/450

FOREIGN PATENT DOCUMENTS

| EP | 1 355 283 A1 | 10/2003 |
| JP | 2002-048589 A | 2/2002 |
| JP | 2002-277528 A | 9/2002 |
| JP | 2004-361363 A | 12/2004 |
| JP | 2006-166421 A | 6/2006 |
| JP | 2006-242578 A | 9/2006 |
| JP | 2011-080934 A | 4/2011 |

OTHER PUBLICATIONS

Extended European Search Report (EESR) dated Jan. 2, 2012 (in English) in counterpart European Application No. 11179556.3.

* cited by examiner

*Primary Examiner* — Edward Raymond
(74) *Attorney, Agent, or Firm* — Holtz, Holtz, Goodman and Chick, PC

(57) ABSTRACT

A positioning apparatus includes: a position measuring section to obtain measured position data by measuring its own present position; a positioning controlling section to control operation timing of the position measuring section to make the position measuring section discontinuously obtain the measured position data; a movement measuring section to measure a movement operation; a moving method judging section to judge a moving method based on a measurement result of the movement measuring section; a map data storage section to store information of a rail route map; and a migration path judging section to judge a migration path in a period judged to be a moving state by an electric train by the moving method judging section based on the measured position data measured by the position measuring section and the information of the rail route map.

7 Claims, 6 Drawing Sheets

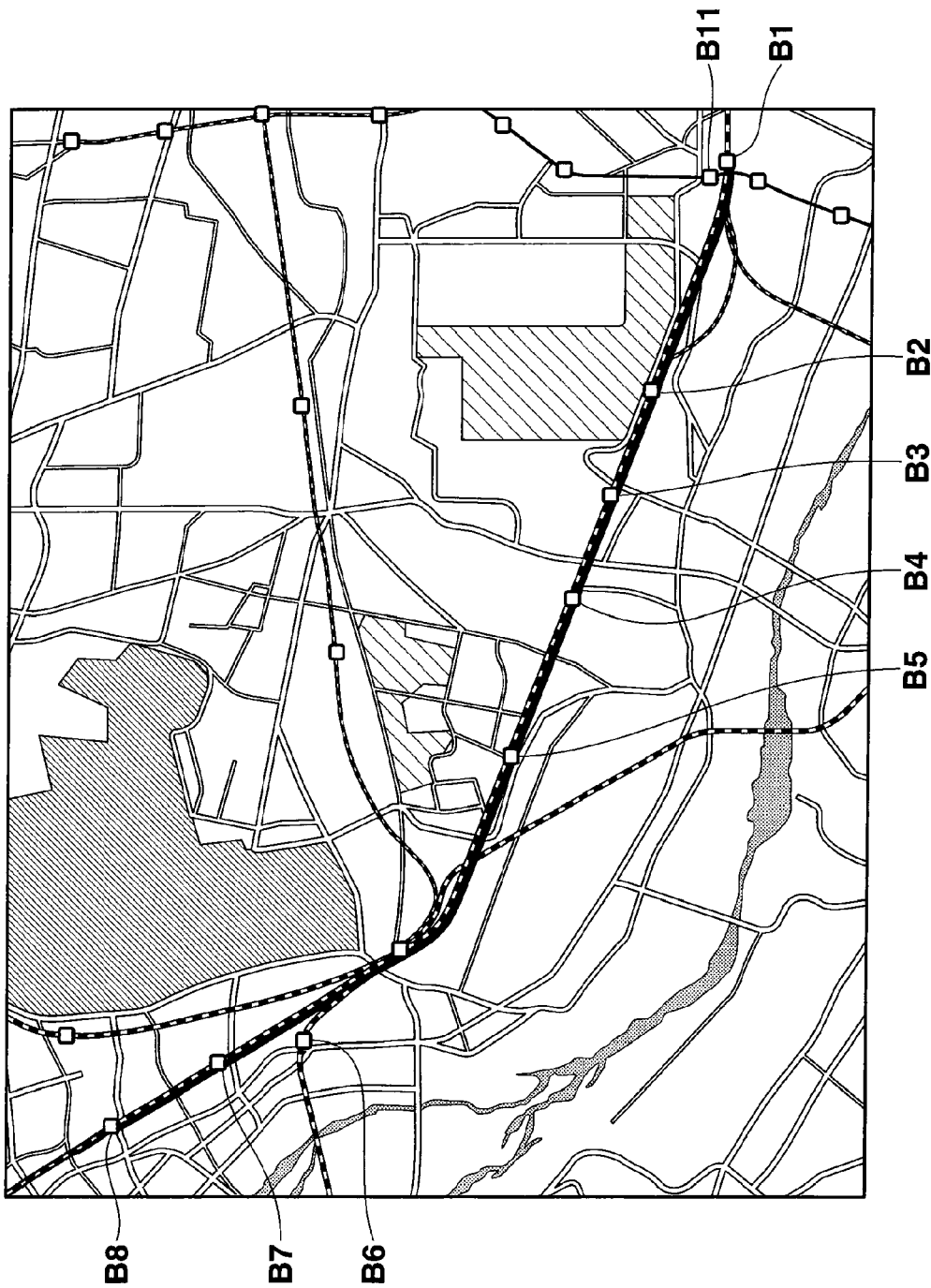

POSITIONING APPARATUS JUDGING MOVING METHOD TO CONTROL POSITIONING TIMING

BACKGROUND OF THE INVENTION

1. Field of the Invention

The present invention relates to a positioning apparatus judging moving method to control positioning timing, a positioning method therefor, and a storage medium.

2. Description of Related Art

There has been a positioning apparatus using a function of positioning an absolute position by using a satellite positioning system, such as a GPS (global positioning system), in conjunction with a function of calculating a position by means of autonomous navigation using a motion sensor equipped with, for example, an acceleration sensor and an azimuth sensor.

By using these functions together, the frequency of receiving electric waves from positioning satellites can be reduced to curtail power consumption.

As the motion sensors for the autonomous navigation function, for example, an acceleration sensor, an angular velocity sensor, an atmospheric pressure sensor, and a magnetic sensor are used.

By extracting the features of the output patterns of these sensors, the positioning apparatus can judge the moving state of a user wearing the positioning apparatus.

For example, Japanese Patent Application Laid-Open Publication No. 2002-48589 discloses the technique of differentiating the means of migration of a mobile object by using the differences of the waveforms of an acceleration sensor and the existence of a vertical direction speed by an atmospheric pressure sensor.

SUMMARY OF THE INVENTION

It is an object of the present invention to provide a low power consumption positioning apparatus capable of obtaining the locus of a migration path including a movement by an electric train with high accuracy, a positioning method therefor, and a storage medium.

In order to achieve at least one of the above objects, according to an aspect of the present invention, there is provided a positioning apparatus, including: a position measuring section to obtain measured position data by measuring its own present position; a positioning controlling section to control operation timing of the position measuring section to make the position measuring section discontinuously obtain the measured position data; a movement measuring section to measure a movement operation; a moving method judging section to judge a moving method based on a measurement result of the movement measuring section; a map data storage section to store information of a rail route map; and a migration path judging section to judge a migration path in a period judged to be a moving state by an electric train by the moving method judging section based on the measured position data measured by the position measuring section and the information of the rail route map.

According to another aspect of the present invention, there is provided a positioning method of obtaining a migration path by using a position measuring section to obtain measured position data by measuring a position, a movement measuring section to measure an operation, and information of a rail route map, the method comprising the steps of: controlling operation timing of the position measuring section to make the position measuring section discontinuously obtain the measured position data; judging a moving method based on a measurement result of the movement measuring section; and judging the migration path in a period of an electric train movement judged at the step of judging a moving method based on position information measured by the position measuring section and the information of the rail route map.

According to another aspect of the present invention, there is provided a storage medium recording a program for a computer to be used for a positioning apparatus, the computer including a position measuring section to obtain measured position data by measuring a position, a movement measuring section to measure an operation, and a map data storage section to store information of a rail route map, the program making the computer function as: a positioning controlling section to control operation timing of the position measuring section to make the position measuring section discontinuously obtain the measured position data; a moving method judging section to judge a moving method based on a measurement result of the movement measuring section; and a migration path judging section to judge a migration path in a period of an electric train movement judged by the moving method judging section based on position information measured by the position measuring section and the information of the rail route map.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 6 is a view showing an example of the measurement of a migration path using an electric train.

DESCRIPTION OF THE PREFERRED EMBODIMENTS

In the following, an embodiment of the present invention will be described with reference to the accompanying drawings.

Figure 1:
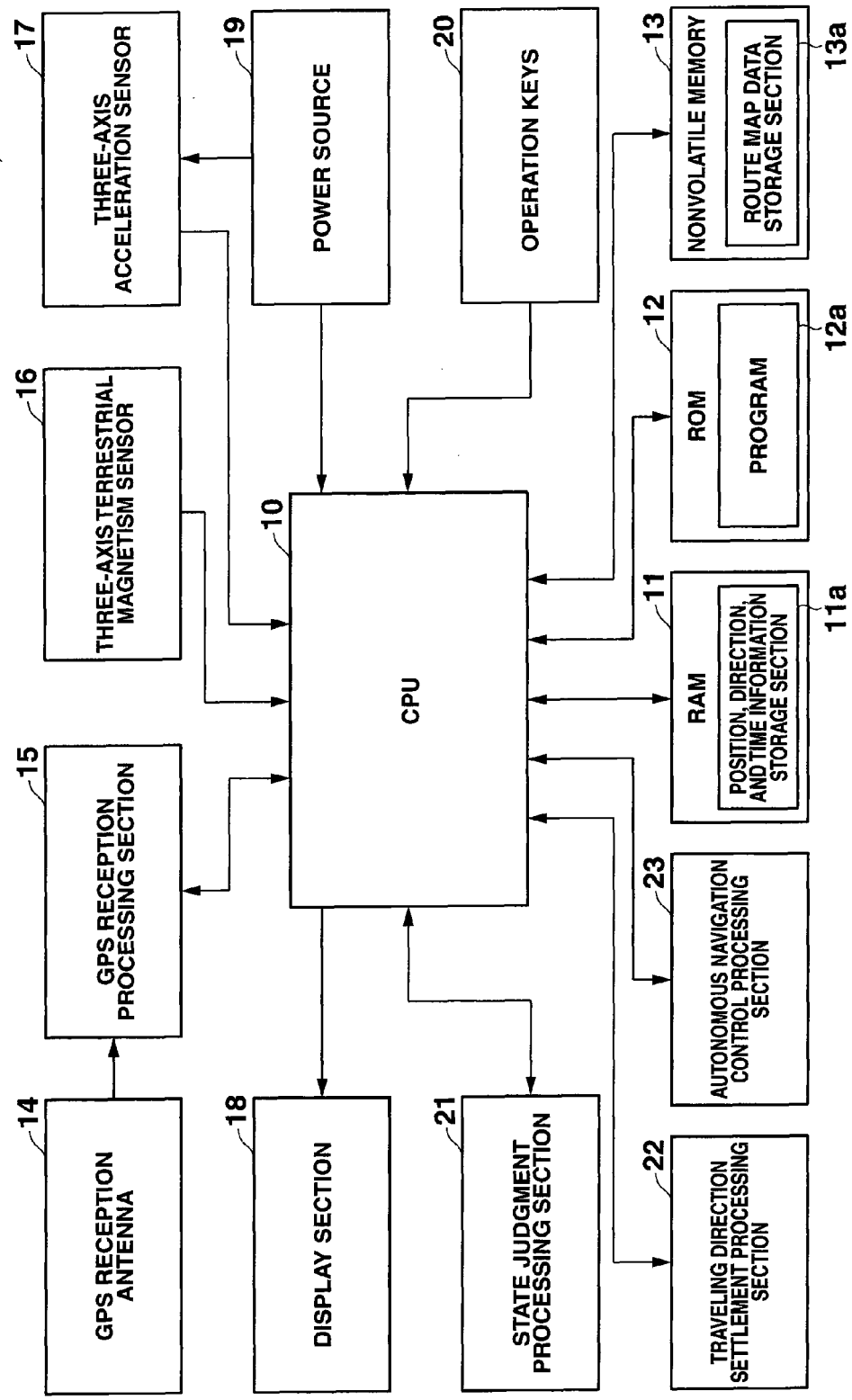
FIG. 1 is a block diagram showing a positioning apparatus of an embodiment of the present invention.

FIG. 1 is a block diagram showing the internal configuration of a positioning apparatus.

The positioning apparatus 1 is a portable positioning apparatus that a user uses by wearing it.

The positioning apparatus 1 includes a CPU (central processing unit) 10 (positioning controlling section) to perform the integrated control of the whole apparatus and arithmetic processing, a RAM (random access memory) 11 to provide a working memory space to the CPU 10, a ROM (read only memory) 12 to store programs to be executed by the CPU 10 and initial data, a nonvolatile memory 13, a GPS reception antenna 14 to receive an electric wave transmitted from a GPS satellite, a GPS reception processing section 15 as a position measuring section to demodulate a received electric wave to perform the decoding processing of the demodulated electric wave, a three-axis terrestrial magnetism sensor 16 to measure three-axis terrestrial magnetism, a three-axis acceleration sensor 17 to measure three-axis direction acceleration, a display section 18 to perform an output display based on an output control signal from the CPU 10, a power source 19 to supply electric power to the CPU 10 and the three-axis acceleration sensor 17, operation keys 20 to convert a user's operational content into a signal to output a converted signal to the CPU 10, a state judgment processing section 21 as a moving method judging section to judge a user's moving method, a traveling direction settlement processing section 22 to judge a user's travelling direction, an autonomous navigation control processing section 23 (position calculating section) to calculate a user's displacement quantity, and the like.

The RAM 11 further includes a position, direction, and time information storage section 11a.

The position, direction, and time information storage section 11a temporarily stores information of a boarding position, a travelling direction, and a boarding time at the time when a boarded electric train starts to move.

The ROM 12 stores a program 12a that the CPU 10 reads out to execute.

The program 12a is, for example, a control program of the positioning apparatus 1 and a positioning processing program.

The program 12a can also be stored in the nonvolatile memory 13.

Alternatively, the program 12a may also be recorded in a portable recording medium, such as a CD-ROM (compact disk read only memory) or a flash memory, to be capable of being executed by the CPU 10 through a reading apparatus.

Moreover, it is also possible to apply a form of being downloaded to the positioning apparatus 1 through a communication line using a carrier wave as a medium to the program 12a.

The nonvolatile memory 13 is, for example, an EEPROM (electrically erasable and programmable read only memory).

The nonvolatile memory 13 includes a route map data storage section 13a (map data storage section).

The route map data storage section 13a stores rail route information, station position information, and the like.

A user can obtain the route map data from the outside as the need arises to update the route map data to the newest information.

Moreover, the nonvolatile memory 13 may be configured to store not only the route map information but also more detailed map data.

The GPS reception processing section 15 demodulates electric waves received through the GPS reception antenna 14 from a plurality of GPS satellites.

Then, the GPS reception processing section 15 obtains the present position based on the demodulated signals from the plurality of GPS satellites and outputs the result to the CPU 10 in accordance with a predetermined format.

The GPS reception processing section 15 intermittently operates based on instructions from the CPU 10.

The three-axis terrestrial magnetism sensor 16 is a sensor capable of measuring a three-axis direction magnetic field by using, for example, a magnetoresistive element.

The terrestrial magnetism is measured by the three-axis terrestrial magnetism sensor 16 and is output to the CPU 10.

The three-axis acceleration sensor 17 is a sensor capable of measuring three-axis direction acceleration.

When a user is in the state of being at a standstill, the three-axis acceleration sensor 17 measures the gravitational acceleration of the earth to output the measurement data to the CPU 10.

The three-axis terrestrial magnetism sensor 16 and the three-axis acceleration sensor 17 constitute a movement measuring section.

The display section 18 is, for example, a LCD (liquid crystal display).

Alternatively, the positioning apparatus 1 may be equipped with a display section of other display systems, such as an organic ELD (electro-luminescent display).

The display section 18 can display the information of, for example, a measured position and a migration path to be superposed on map data read out from the nonvolatile memory 13 based on a signal from the CPU 10.

The state judgment processing section 21 obtains measurement data by the three-axis terrestrial magnetism sensor 16 and the three-axis acceleration sensor 17 through the CPU 10, and judges the operation state of a user wearing the positioning apparatus 1 based on arithmetic results using the measurement data.

The states capable of being judged by the state judgment processing section 21 of the present embodiment include a stopping state, a walking state, and a moving state using an electric train, of a user.

Furthermore, it may be enabled to judge the moving state by means of an automobile, a bicycle, or the like, and the moving state by means of an escalator, a moving sidewalk, or the like, or it may be enabled to judge a walking state and a running state.

The judgment of a walking state and a moving state by means of an electric train can be performed as follows based on the measurement of three-axis terrestrial magnetism sensor 16 and the three-axis acceleration sensor 17.

First, in case of a walking state, the state judgment processing section 21 can determine respective movements in the vertical direction and the travelling direction from certain gravitational acceleration and the direction of the terrestrial magnetism obtained from the inputs of both sensors 16 and 17.

Because the gravity center of a user wearing the positioning apparatus 1 moves in the vertical direction every step during walking, the periodic changes of the vertical direction acceleration can be measured.

In the case of a movement by means of an electric train, the magnetic field in a vehicle is first disturbed owing to the operation of the motor of the electric train, and the output of the three-axis terrestrial magnetism sensor 16 continues to unstably change.

On the other hand, the travelling direction becomes incapable of being identified when the output of the three-axis terrestrial magnetism sensor 16 is disturbed, but the output of the three-axis acceleration sensor 17 changes in a plane perpendicular to the gravitation direction by the acceleration at the time of the starting of the electric train.

Moreover, while the electric train is moving, the acceleration changes characteristic of the movement of an automobile cannot be observed in almost the perpendicular direction to that of the acceleration at the time of the starting of the electric train in the horizontal plane.

Concretely, in the case of a movement by an automobile, characteristic vibrations of 1-3 Hz in the direction perpendicular to a travelling direction can be observed in the horizontal plane, but these vibrations do not produced in a movement by an electric train.

A movement by an electric train can accordingly be identified by performing the Fourier transformation of the data in a horizontal plane among the outputs of the three-axis acceleration sensor 17 to obtain the amplitude intensity of this frequency band, and by comparing the amplitude intensity with a predetermined threshold value.

After entering the moving state by an electric train, the traveling direction settlement processing section 22 performs the processing of judging the route to be traveled by the electric train and the travelling direction thereof while referring to the data of a route map by using the initial position data and the position data after starting the movement by the electric train.

The traveling direction settlement processing section 22 and the CPU 10 constitute a migration path judging section.

The autonomous navigation control processing section 23 obtains the measurement data of the three-axis terrestrial magnetism sensor 16 and the three-axis acceleration sensor 17 through the CPU 10, and calculates a moving direction and a movement distance of a user based on the measurement data.

In the positioning apparatus 1 of the present embodiment, the autonomous navigation control processing section 23 calculates a movement distance in a walking state of a user.

Next, an operation procedure of positioning processing of the present invention will be described with reference to the accompanying flow charts.

Figure 2:
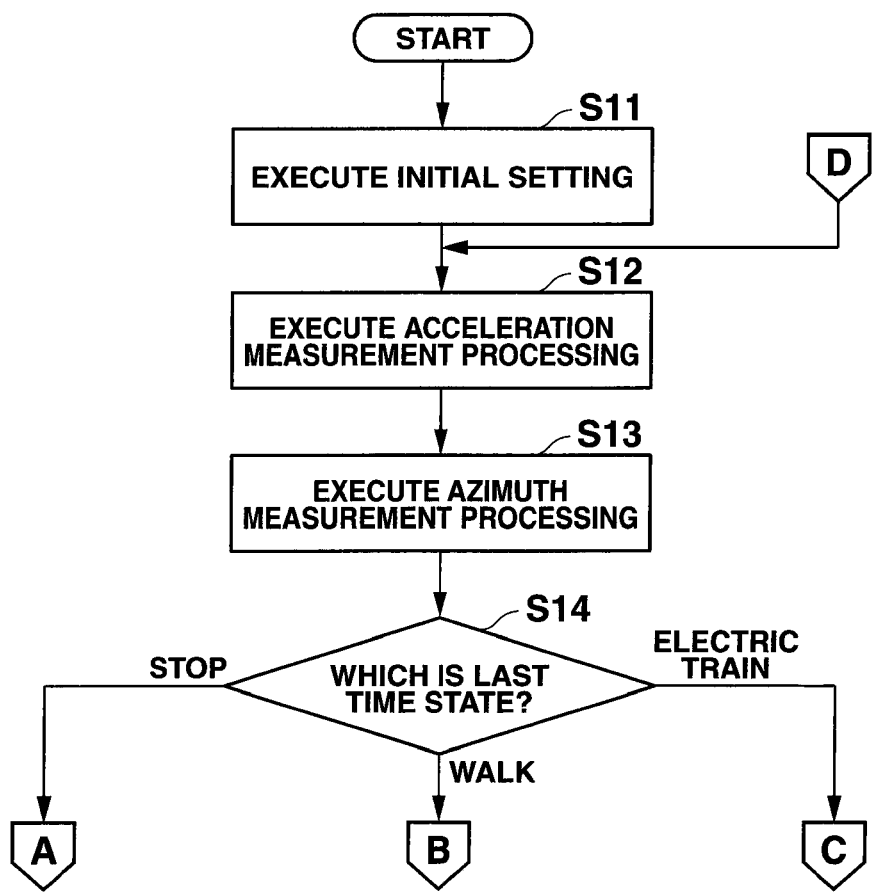
FIG. 2 is a first portion of the flow chart of positioning processing.

FIG. 2 is a flow chart showing the control procedure of the positioning processing executed by the CPU 10.

Figure 3:
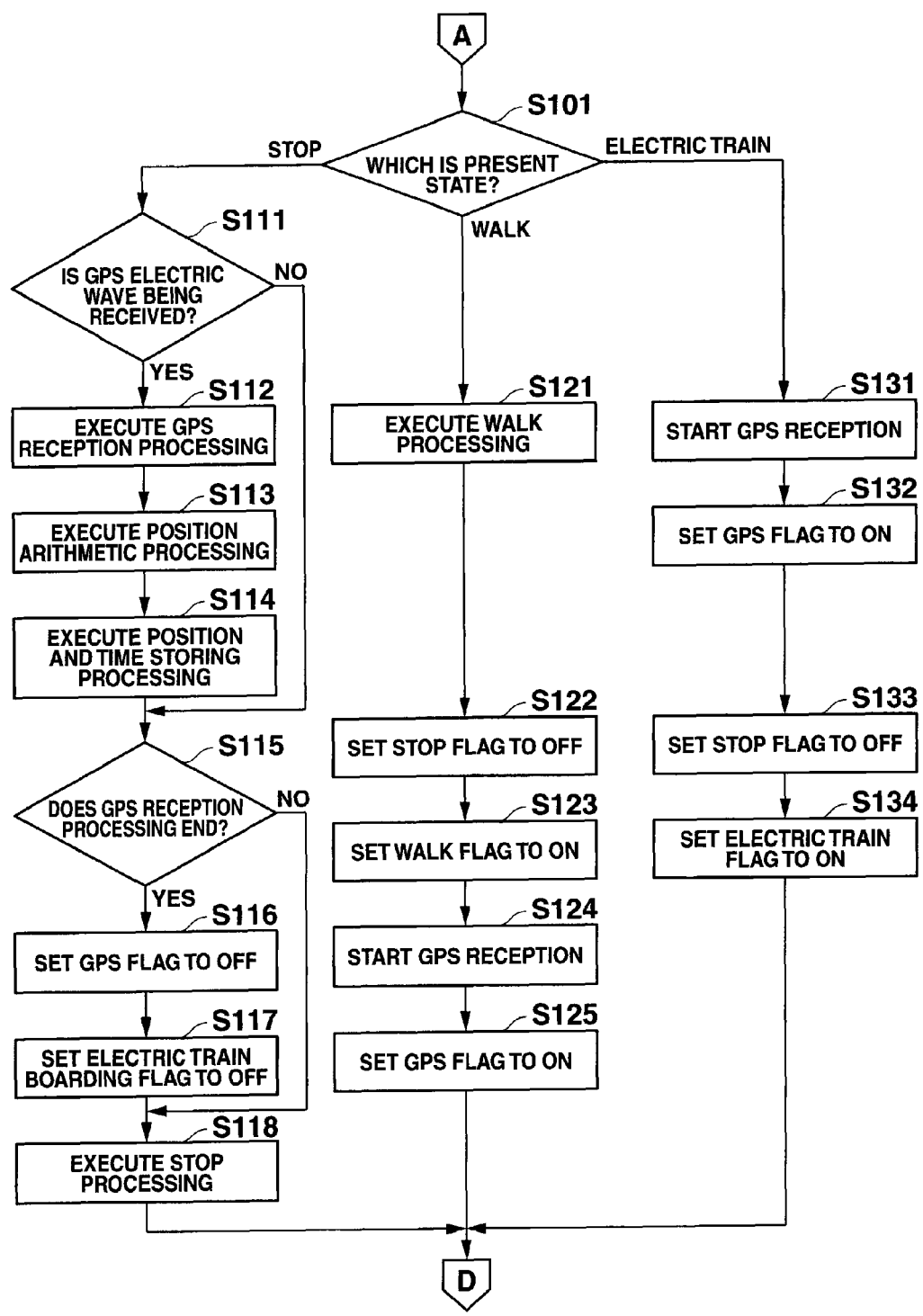
FIG. 3 is a second portion of the flow chart of the positioning processing.
Figure 4:
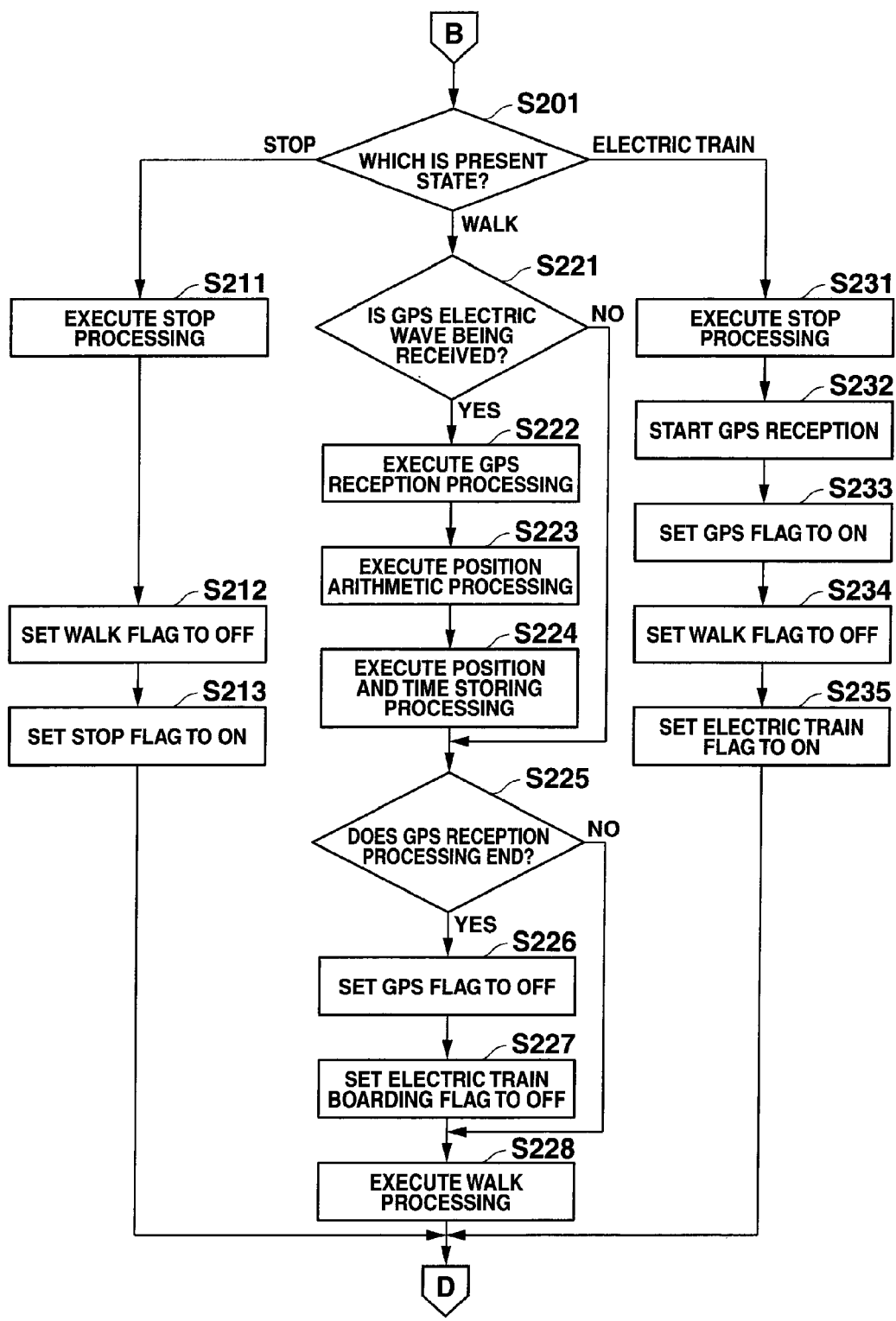
FIG. 4 is a third portion of the flow chart of the positioning processing.
Figure 5:
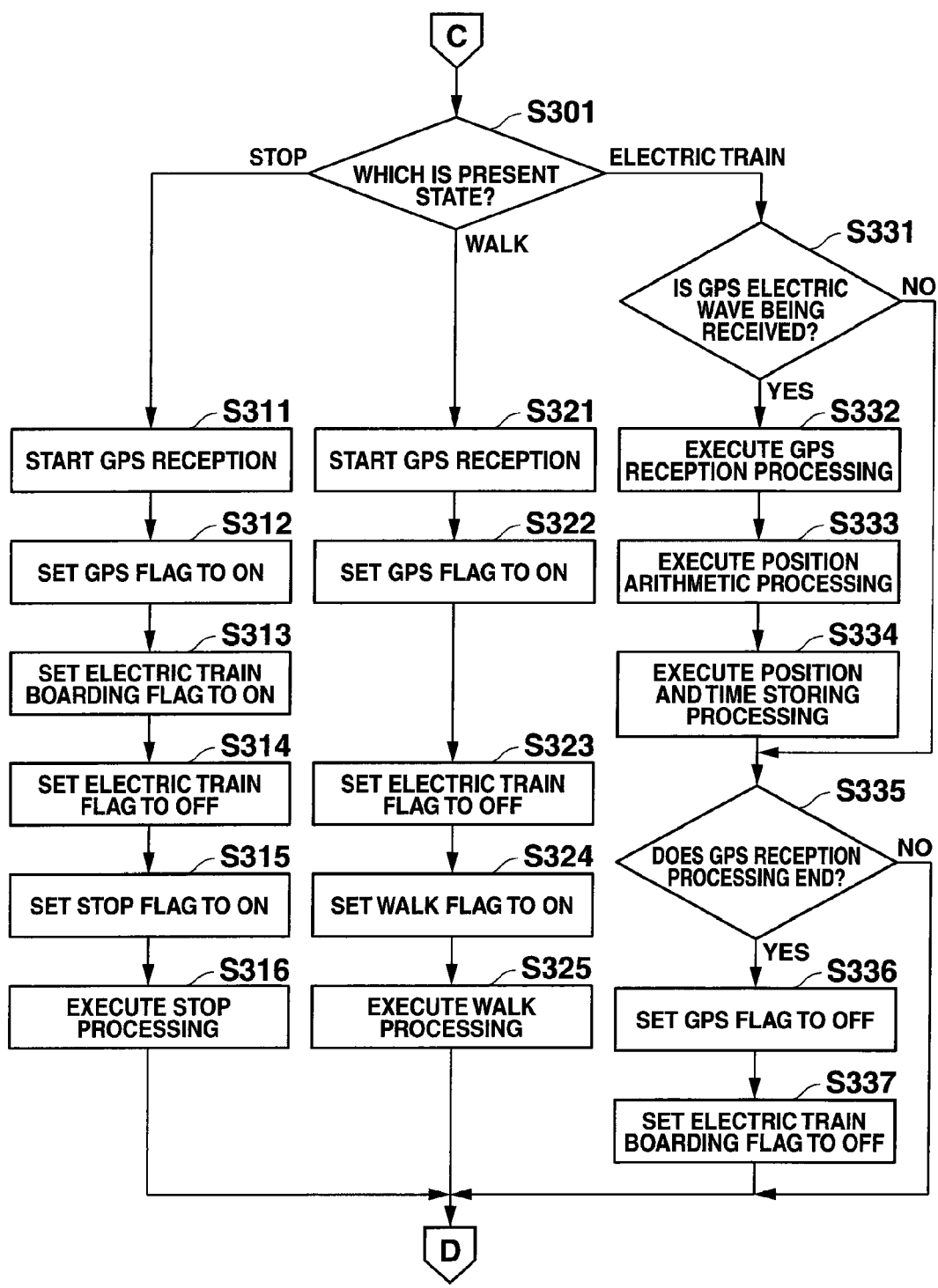
FIG. 5 is a fourth portion of the flow chart of the positioning processing.

Moreover, FIGS. 3-5 are flowcharts showing the control procedures of processing after a stop, processing after a walk, and processing after an electric train, respectively, each of which will be called in the flow chart of FIG. 2.

The control processing of the positioning processing is started based on an input signal from the operation keys 20.

When the control processing is started, the CPU 10 first performs initial setting as shown in FIG. 2 (Step S11).

Concretely, the CPU 10 makes the GPS reception processing section 15 operate to obtain the data of its own present position.

Moreover, the CPU 10 obtains a judgment result of the operation state of a user from the state judgment processing section 21.

When it is judged that the operation state is a stopping state, the CPU 10 sets a stop flag "ON".

When it is judged that the operation state is a walking state, the CPU 10 sets a walk flag "ON".

Moreover, when it is judged that the operation state is an electric train moving state, the CPU 10 sets an electric train flag "ON".

Next, the CPU 10 transmits the acceleration data in a predetermined period among the pieces of measurement data input from the three-axis acceleration sensor 17 to the state judgment processing section 21 (Step S12).

Moreover, the CPU 10 transmits the terrestrial magnetism data in the predetermined period among the pieces of measurement data input from the three-axis terrestrial magnetism sensor 16 to the state judgment processing section 21 (Step S13).

The CPU 10 performs judgment processing based on a user's operation state obtained from the state judgment processing section 21 at the last time (at the initial setting (Step 11) at the first time) (Step S14).

The CPU 10 performs the judgment processing by ascertaining which of the stop flag, the walk flag, and the electric train flag is "ON".

When it is judged that the operation state at the last time is the stopping state, the CPU 10 moves the present processing to the processing after a stop from Step S101.

When it is judged that the operation state at the last time is the walking state, the CPU 10 moves the present processing to the processing after a walk from Step S201.

Moreover, when it is judged that the operation state at the last time is the moving state by an electric train, the CPU 10 moves the present processing to the processing after an electric train from Step S301.

When the present processing has moved to that at Step S101, the CPU 10 transmits a signal to the state judgment processing section 21 to make the state judgment processing section 21 judge a user's present operation state based on the acceleration data and the terrestrial magnetism data transmitted to the state judgment processing section 21 at Steps S11 and S12, as shown in FIG. 3.

Then, the CPU 10 obtains the judgment result of the operation state from the state judgment processing section 21 and performs the judgment processing of the obtained operation state.

When it is judged that the present operation state is the stopping state continuously from the last time in the judgment processing at Step S101, the CPU 10 judges whether the GPS reception processing section 15 is performing the reception processing of an electric wave from a GPS satellite (Step S111).

The existence of the reception processing by the GPS reception processing section 15 is indicated by whether a GPS flag is "ON" or "OFF".

When it is judged that the GPS reception processing section 15 is performing the reception processing of the electric wave from the GPS satellite, the CPU 10 makes the GPS reception processing section 15 continuously perform the GPS reception processing (Step S112).

Moreover, the CPU 10 performs position arithmetic processing by using the received and demodulated signal from the GPS satellite (Step S113).

The CPU 10 obtains the result of the position arithmetic processing, which result is output from the GPS reception processing section 15, and makes the position, direction, and time information storage section 11a store the obtained position and the obtained time (Step S114).

Then, the CPU 10 moves the present processing to that at Step S115.

On the other hand, when it is judged that the GPS reception processing section 15 is not performing the reception processing of any electric waves from any GPS satellites in the judgment processing at Step S111, the CPU 10 branches the present processing to the "NO" branch, and omits the processing at Steps S112-S114 to move the present processing to that at Step S115.

Next, the CPU 10 judges whether the GPS reception processing has ended or not.

When it is judged that the reception processing by the GPS reception processing section 15 is not being performed and that the GPS reception processing has already ended, the CPU 10 sets the GPS flag "OFF" (Step S116), and sets an electric train boarding flag "OFF" (Step S117).

Then, the CPU 10 moves the present processing to that at Step S118.

When it is judged that the GPS reception processing has not ended, for example, in the case where the reception processing is repeatedly being executed in the state in which necessary number of satellite electric waves are not received, the CPU 10 moves the present processing to that at Step 118 with the GPS flag being "ON" as it is.

The CPU 10 executes stop processing (Step S118).

In the stop processing, the CPU 10 stops the calculation of the displacement quantity and the moving direction in the autonomous navigation control processing section 23.

Then, the CPU 10 returns the present processing to that at Step S12.

When it is judged that the present operation state is a walking state in the judgment processing at Step S101, the CPU 10 executes walk processing (Step S121).

In this walk processing, the CPU 10 makes the autonomous navigation control processing section 23 operate to obtain autonomously measured present position data.

Then, the CPU 10 makes the position, direction, and time information storage section 11a store the present position data, and transmits a signal to the display section 18 to make the display section 18 display the present position on the display screen thereof.

Next, the CPU 10 sets the stop flag "OFF" (Step S122), and sets the walk flag "ON" (Step S123).

Then, the CPU 10 executes GPS reception start processing (Step S124), and sets the GPS flag "ON" (Step S125).

Then, the CPU 10 returns the present processing to that at Step S12.

When it is judged that the present operation state is a moving state by an electric train in the judgment processing at Step S101, the CPU 10 next transmits a signal to the GPS reception processing section 15 to make the GPS reception processing section 15 start GPS reception processing (Step S131) and to set the GPS flag "ON" (Step S132).

Next, the CPU 10 sets the stop flag "OFF" (Step S133), and sets the electric train flag "ON" (Step S134).

Then, the CPU 10 returns the present processing to that at Step S12.

When it is judged that the last time operation state is a walking state in the judgment processing at Step S14 (that is, the walk flag is "ON"), the CPU 10 moves the present processing to that at Step S201.

Then, as shown in FIG. 4, the CPU 10 obtains a user's present operation state from the state judgment processing section 21.

Then, the CPU 10 performs the judgment processing of the operation state.

When it is judged that the present operation state is a stopping state in the judgment processing at Step S201, the CPU 10 performs stop processing (Step S211), and stops the processing of the autonomous navigation control processing section 23 which processing is made to be executed in the period of the walking state.

Then, the CPU 10 sets the walk flag "OFF" (Step S212), and sets the stop flag "ON" (Step S213).

Then, the CPU 10 returns the present processing to that at Step S12.

When it is judged that the present operation state is continuously the walking state in the judgment processing at Step S201, the CPU 10 judges whether the GPS reception processing section 15 is performing the reception processing of an electric wave from a GPS satellite or not (Step S221).

When it is judged that the GPS reception processing section 15 is performing the reception processing of the electric wave from the GPS satellite, the CPU 10 makes the GPS reception processing section 15 continuously perform the GPS reception processing (Step S222), and uses the received and demodulated signal from the GPS satellite to make the GPS reception processing section 15 perform position arithmetic processing (Step S223).

The CPU 10 obtains a position arithmetic result output from the GPS reception processing section 15 to make the position, direction, and time information storage section 11a store the position information and the time information (Step S224).

Then, the CPU 10 moves the present processing to that at Step S225.

On the other hand, when it is judged that the GPS reception processing section 15 is not performing any reception processing of any electric waves from any GPS satellites in the judgment processing at Step S221, the CPU 10 branches the present processing to the "NO" branch, and omits the processing at Steps S222-S224 to move the present processing to that at Step S225.

Next, the CPU 10 judges whether the GPS reception processing has ended or not (Step S225).

When it is judged that no reception processing by the GPS reception processing section 15 is being performed and the GPS reception processing has already ended, the CPU 10 sets the GPS flag "OFF" (Step S226).

Moreover, the CPU 10 sets the electric train boarding flag "OFF" (Step S227).

Then, the CPU 10 moves the present processing to that at Step S228.

When it is judged that the GPS reception processing has not ended, the CPU 10 omits the processing at Steps S226-S227 to move the present processing to that at Step S228.

The CPU 10 executes walk processing (Step S228).

While the walking state is continuing, the CPU 10 makes the autonomous navigation control processing section 23 calculates displacement quantities and moving directions, and makes the GPS reception processing section 15 operate to obtain and update position data to be used as references of autonomous navigation at predetermined time intervals.

Moreover, the CPU 10 makes the display section 18 display the obtained data of the positions and the migration paths.

Then, the CPU 10 returns the present processing to that at Step S12.

When it is judged that the present operation state is a moving state by an electric train in the judgment processing at Step S201, the CPU 10 sets this timing as the one at which a movement by an electric train is started (Step S231).

The CPU 10 first executes stop processing to stop the autonomous navigation processing executed by the autonomous navigation control processing section 23 during walking.

Moreover, the CPU 10 makes the display section 18 display the fact that a user is now moving by an electric train.

Next, the CPU 10 sends an instruction to the GPS reception processing section 15 to make the GPS reception processing section 15 start GPS reception processing, and starts the obtainment operation of the data of the movement start position of the electric train.

The CPU 10 sets the GPS flag "ON" (Step S233), sets the walk flag "OFF" (Step S234), and sets the electric train flag "ON" (Step S235).

When it is judged that the last time operation state is a moving state by an electric train in the judgment processing at Step S14 (that is, the electric train flag is "ON"), the CPU 10 moves the present processing to that at Step S301.

Then, the CPU 10, as shown in FIG. 5, transmits a signal to the state judgment processing section 21, and obtains the present operation state of the user from the state judgment processing section 21 to perform the judgment processing of this operation state.

When it is judge that the present operation state is a stopping state in the judgment processing at Step S301, the CPU 10 moves the present processing to that at Step S311.

In this case, it is judged that the user did not get off the electric train when the electric train stopped and the user is being on the electric train as he or she is.

The CPU 10 transmits an instruction to the GPS reception processing section 15 to make the GPS reception processing section 15 start the reception processing of the electric waves from GPS satellites, and sets the GPS flag "ON" (Step S312).

Moreover, the CPU 10 sets the electric train boarding flag "ON" (Step S313), sets the electric train flag "OFF" (Step S314), and furthermore sets the stop flag "ON" (Step S315).

The CPU 10 performs stop processing to continue the spotting state of the processing of the autonomous navigation control processing section 23, and makes the display section 18 display the fact that the user is in a stopping state in the electric train now (Step S316).

Then, the CPU 10 returns the present processing to that at Step S12.

When it is judged that the present operation state is a walking state in the judgment processing at Step S301, the CPU 10 moves the present processing to that at Step S321.

In this case, the CPU 10 judges that the user got off the electric train after the electric train had stopped, and the CPU 10 starts to obtain the information of the getting-off position.

The CPU 10 transmits an instruction to the GPS reception processing section 15 to make the GPS reception processing section 15 start the reception processing of the electric waves from the GPS satellites, and set the GPS flag "ON" (Step S322).

Moreover, the CPU 10 sets the electric train flag "OFF" (Step S323), and sets the walk flag "ON" (Step S324).

Then, the CPU 10 performs walk processing (Step S325).

The CPU 10 makes the autonomous navigation control processing section 23 start the calculation processing of displacement quantities and moving directions, and after that, the CPU 10 returns the present processing to that at Step S12.

When it is judged that the present operation state is continuously in the moving state by an electric train in the judgment processing at Step S301, the CPU 10 first judges whether the GPS reception processing section 15 is performing the reception processing of an electric wave from a GPS satellite or not (Step S331).

When it is judged that the GPS reception processing section 15 is performing the reception processing of the electric wave from the GPS satellite, the CPU 10 makes the GPS reception processing section 15 continuously perform the reception processing (Step S332), and makes the GPS reception processing section 15 perform position arithmetic processing by using the signal generated by receiving the electric wave from the GPS satellite and by demodulating the received electric wave (Step S333).

The CPU 10 obtains the position arithmetic result output from the GPS reception processing section 15, and makes the position, direction, and time information storage section 11*a* store the position information and the time information (Step S334).

Then, the CPU 10 moves the present processing to the judgment processing at Step S335.

On the other hand, when it is judged that the GPS reception processing section 15 is not performing any reception processing of any electric waves from any GPS satellites in the judgment processing at Step S331, the CPU 10 branches the present processing to the "NO" branch, and omits the processing at Steps S332-S334 to move the present processing to the judgment processing at Step S335.

In the judgment processing at Step S335, the CPU 10 judges whether the GPS reception processing has ended or not.

When it is judged that the reception processing by the GPS reception processing section 15 is not performed and the GPS reception processing has already ended, the CPU 10 sets the GPS flag "OFF" (Step S336), and sets the electric train boarding flag "OFF" (Step S337).

Then, the CPU 10 returns the present processing to that at Step S12.

When it is judged that the GPS reception processing has not ended yet in the judgment processing at Step S335, the CPU 10 returns the present processing to that at Step S12 as it is.

Next, a concrete operation example of the positioning control processing described above when it is executed at the time of a movement by means of an electric train will be described with reference to the flow charts.

FIG. 6 is a view showing a concrete example of a positioning result at the time of the movement by means of the electric train in the present embodiment.

When a user of the positioning apparatus 1 boards an electric train at a station B1 and the electric train is set into motion, the judgment result of the operation state obtained from the state judgment processing section 21 by the CPU 10 changes from a walking state to the moving state by the electric train (Steps S14 and S201).

By this change, the CPU 10 judges that the user has boarded on the electric train.

The CPU 10 performs stop processing to make the autonomous navigation control processing section 23 stop autonomous navigation (Step S231), and transmits an instruction to the GPS reception processing section 15 to make the GPS reception processing section 15 start GPS reception processing (Step S232).

Successively, the CPU 10 sets the GPS flag "ON" (Step S233), sets the walk flag "OFF" (Step S234), and changes the electric train flag to "ON" (Step S235).

Alternatively, when there is a stoppage time from the user's boarding to the departure of the electric train, the judgment result of the operation state obtained from the state judgment processing section 21 changes from a walking state to the moving state by the electric train through a stopping state.

In this case, the CPU 10 first executes the stop processing at the time point when the judgment result changes to the stopping state (Steps S14 and S201) to make the autonomous navigation control processing section 23 stop the autonomous navigation (Step S211).

Then, the CPU 10 sets the walk flag "OFF" (Step S212), and sets the stop flag "ON" (Step S213).

The judgment result of a stopping state is repeatedly obtained from the state judgment processing section 21 during a period of from the change to the stopping state to the departure of the electric train (Steps S14 and S101).

In this period, the GPS flag is "OFF" (Step S111), and the CPU 10 accordingly repeats only the stop processing (Step S117).

When the electric train departs, the judgment result of the operation state which judgment result is input from the state judgment processing section 21 into the CPU 10 changes from the stopping state to the moving state by the electric train (Steps S14 and S101).

In this case, the CPU 10 judges that the user has boarded on the electric train at the time of the previous walking state.

The CPU 10 transmits an instruction to the GPS reception processing section 15 to start GPS reception processing (Step S131), and sets the GPS flag "ON" (Step S132).

Moreover, the CPU 10 sets the stop flag "OFF" (Step S133), and sets the electric train flag "ON" (Step S134).

As the boarded electric train continues to travel, the judgment result of the operation state which judgment result is input from the state judgment processing section 21 continues to be the moving state by the electric train (Steps S14 and S301).

GPS reception processing, position arithmetic processing, and position and time storing processing are each executed until the GPS reception processing that has started at Steps S231 and S132 ends (Steps S331-S334).

The position data obtained at this time and stored in the position, direction, and time information storage section 11a is boarding place data.

On the other hand, when the GPS reception processing ends, the CPU 10 sets the GPS flag "OFF" (Steps S335 and S336), and does not obtain any position data on and after that while the electric train is travelling.

Moreover, the CPU 10 again sets the electric train boarding flag "OFF" (Step S337).

Here, even if the user moves in the electric train while the train is moving, it can be judged that the movement of the electric train has not end yet by the outputs of the three-axis terrestrial magnetism sensor 16, and the operation state input from the state judgment processing section 21 does not change to a walking state.

When the electric train arrives at each of stations B2-B7 on the way and stops there, the judgment result of the operation state input from the state judgment processing section 21 changes from the moving state by the electric train to a stopping state (Step S14 and S301).

The CPU 10 transmits an instruction to the GPS reception processing section 15 to make the GPS reception processing section 15 start GPS reception processing (Step S311), and sets the GPS flag "ON" (Step S312).

Moreover, the CPU 10 sets the electric train boarding flag "ON," sets the electric train flag "OFF," and furthermore sets the stop flag "ON" (Steps S313-S315).

Then, the CPU 10 performs stop processing (Step S316).

When the electric train starts from each of the stations B2-B7 on the way, the judgment result of the operation state input from the state judgment processing section 21 into the CPU 10 changes from the stopping state to the moving state by the electric train (Steps S14 and S101).

At this time, the GPS reception processing has already been started (Step S131), and the GPS flag has already been set "ON" (Step S132).

Then, the CPU 10 sets the stop flag "OFF" (Step S133), and sets the electric train flag "ON" (Step S134).

As the boarded electric train continues to travel, the judgment result of the operation state which judgment result is input from the state judgment processing section 21 continues to be the moving state by the electric train (Steps S14 and S301).

GPS reception processing, position arithmetic processing, and position and time storing processing are each executed until the GPS reception processing that has been started at Steps S231 and S132 ends (Steps S331-S334).

When the GPS reception processing ends, the CPU 10 sets the GPS flag "OFF" (Steps S335 and S336), and sets the electric train boarding flag "OFF" again (Step S337).

The traveling direction settlement processing section 22 settles the travelling direction from the station where the user has boarded the electric train based on the position data of the station and the data of the present position obtained by the GPS reception processing.

When the electric train has arrived at a station B8 and the user gets off the train, the judgment result of the operation state which judgment result is input from the state judgment processing section 21 into the CPU 10 changes from the moving state by the electric train to a walking state (Steps S14 and S101).

It is judged by this change that the user has gotten off the electric train.

First, the GPS reception processing section 15 starts GPS reception processing (Step S321).

Then, the CPU 10 sets the GPS flag "ON", sets the electric train flag "OFF," and sets the walk flag "ON" (Steps S322-S324).

Moreover, the CPU 10 executes walk processing, and transmits an instruction to the autonomous navigation control processing section 23. Thereby, the CPU 10 makes the autonomous navigation control processing section 23 start the measurement of displacement quantities and moving directions, and performs GPS reception starting processing at predetermined time intervals (Step S325).

Here, when the user has moved in the train during stopping at stations B2-B7 on the way, the movements are regarded as that of once getting off the electric train and boarding the electric train again, and similar processing is performed.

When an waling state is continued after the user has gotten off at the station B8 (Steps S14 and S201), GPS reception processing, position arithmetic processing, and position and time storing processing are executed because the GPS flag is "ON" at the beginning (Steps S221-S224).

Then, the position data obtained by means of a GPS satellite and stored in the position, direction, and time information storage section 11a is used as the position data for identifying the station where the user got off the electric train.

When the GPS reception processing ends, the CPU 10 sets the GPS flag "OFF," and sets also the electric train boarding flag "OFF" (Steps S225-S227).

Then, walk processing is performed (Step S228).

At the time of getting off the electric train, the autonomous navigation control processing section 23 is in the state of having no position data as a reference, and the autonomous navigation control processing section 23 calculates back the position data of the station where the user got off the electric train based on the position data obtained by the GPS reception processing and the measurement data of the displacement quantities and the moving directions which measurement has been executed from the getting-off time point.

Then, the CPU 10 determines the route used for the electric train movement and the section of the route based on the position data of the boarding place and the getting-off place that are stored in the position, direction, and time information storage section 11a, and route map data stored in the route map data storage section 13a.

Moreover, in the case where a plurality of paths exists or the like, the CPU 10 selects a path by also referring to the data of the travelling direction obtained at the station B2 and the position data of the stations B2-B7 on the way.

Alternatively, when a user has started a walking operation to get off the electric train after the electric train has arrived at the station B8 and stopped for a while, the judgment result input from the state judgment processing section 21 into the CPU 10 changes from the moving state by the electric train to a walking state through a stopping state.

In this case, the CPU 10 first starts GPS reception processing at the stage at which the judgment result of the state judgment processing section 21 moves to the stopping state (Steps S311-S312). Then, the CPU 10 sets the electric train flag "OFF," and sets the electric train boarding flag and the stop flag "ON" (Steps S313-S315).

Moreover, the CPU 10 performs stop processing (Step S316).

After that, when the user has started a walking operation and gets off the electric train (Steps S14 and S101), the CPU 10 first performs walk processing and makes the autonomous navigation control processing section 23 start autonomous navigation (Step S121).

Moreover, the CPU 10 sets the stop flag "OFF" and sets the walk flag "ON" (Steps S122-S123).

The CPU 10 has already started the execution of the next GPS reception start processing (Step S124), and the CPU 10 has already set the GPS flag "ON" (Step S125).

Then, when the judgment result input from the state judgment processing section 21 into the CPU 10 continuously becomes the walking state (Steps S14 and S201), the GPS flag is "ON" at the beginning, and the CPU 10 executes GPS reception processing, position arithmetic processing, and position and time storing processing (Steps S221-S224).

Then, when the GPS reception processing ends, the CPU 10 changes the GPS flag and the electric train boarding flag to be "OFF" (Steps S225-S227).

Moreover, the CPU 10 repeatedly executes the walk processing and performs autonomous navigation (Step S228).

As described above, the positioning apparatus 1 of the embodiment described above includes the route map data storage section 13a, and judges the moving state of an electric train based on the waveform pattern of the three-axis acceleration sensor 17. Thereby, even in the state in which the frequency of performing the measurement processing of positions using the GPS reception processing section 15 is decreased, the positioning apparatus 1 can specify the migration path of the electric train by performing the comparison with route map data.

Consequently, the positioning apparatus 1 can suppress the consumption quantity of electric power.

Moreover, the positioning apparatus 1 can obtain accurate migration path information by obtaining the migration path by using route map data in conjunction with the position data of limited points when an electric train runs on a limited track, such as a rail route, even if troublesome operations, such as matching processing of roads and routes on a map with real ones at each place of a migration path, are omitted.

Moreover, the positioning apparatus 1 can obtain accurate migration path information without increasing the frequency of position measurement by a satellite positioning system using GPS satellites by specifying a station where a user has boarded an electric train and a station where the user has gotten off the electric train by using map data at the time of the movement by the electric train, and by identifying the migration path even if no autonomous navigation functions can be used owing to the influences of the magnetic fields generated by a motor of the electric train, or even if a positioning apparatus that is not equipped with any autonomous navigation functions is used.

Moreover, the positioning apparatus 1 can efficiently obtain the information of a station where a user has boarded an electric train, a station where the user has gotten off the electric train, and a highly accurate migration path by limiting the measurement processing of a position by the GPS reception processing section 15 to be executed only at the time when a movement by the electric train is started and at the time when the electric train stops.

Here, although the positioning apparatus 1 determines a route path of an electric train movement based on the position data of a boarding place and a getting-off place only when it is judged that a user has gotten off the electric train in the above embodiment, the positioning apparatus 1 may determine a route path every stop.

The positioning apparatus 1 can more accurately obtain a route by making the information of way stations be included at the time of determining a migration path even if there is a plurality of routes.

Moreover, the positioning apparatus 1 can make a route map stored in the route map data storage section 13a hold not only the information as a mere map but also the information of each operation route in addition.

Even if, for example, the correct station B1 where a user has boarded an electric train cannot be discriminated from an adjacent station Ell when the accuracy of a measured station position is not so good, the positioning apparatus 1 can also discriminate the station where the user has boarded the electric train because only the station B1 is connected to the station B8 where the user has gotten off the electric train on the route.

Moreover, the positioning apparatus 1 can select one of parallel routes based on, for example, the information of the existence of an electric train performing a through operation even if railroad tracks are connected.

Moreover, although the embodiment described above identifies a station where a user has boarded an electric train and a station where the user has gotten off the electric train based on the position data obtained by using GPS satellites, the positioning apparatus 1 can also identify a station by using the position data by autonomous navigation using the places measured by using the GPS satellites performed before user's boarding and after user's getting-off as references.

By using the positioning using the GPS satellites in conjunction with autonomous navigation in such a way, the positioning apparatus 1 can similarly select a migration path of an electric train by using a route map even in the case where it is difficult to obtain the position data by GPS reception processing in an underground station or a station in a building.

Moreover, the positioning apparatus 1 of the embodiment described above performs or sometimes ends the GPS reception processing at Steps S111-S117 during stopping states when a stoppage time of an electric train at each of the stations B2-B7 on the way is long, or when a period of from a time when the electric train has arrived at the station B8 where the user has gotten off the electric train to a time when the user has started to get off the electric train is long.

In this state, the positioning apparatus 1 can be configured not to perform the GPS reception start processing at Steps S124 and S131 and the processing of setting the GPS flag "ON" at Steps S125 and S132 by previously setting an operation flag of the reception processing at the time when an electric train is stopping.

[Modification 1]

The internal configuration of the positioning apparatus of a modification 1 is the same as that of the positioning apparatus 1 of the embodiment described above, and the description thereof is omitted.

The positioning apparatus 1 of the modification 1 does not start GPS reception processing when a user moves from a moving state by an electric train to a stopping state.

That is, the positioning apparatus 1 of the modification 1 does not perform the processing at Steps S311 and S312 of FIG. 5.

Moreover, when the sate of a user changes from a stopping state to a moving state by an electric train, the CPU 10 does not perform the GPS reception start processing and the processing of setting the GPS flag "ON" (Steps S131 and S132), but performs the processing of setting the electric train boarding flag "OFF" in place of the former processing when the electric train boarding flag is "ON."

In the positioning apparatus 1 of the modification 1, the CPU 10 holds the GPS flag "OFF" when the state of a user moves from a moving state by an electric train to a stopping state.

After that, if it is judged that the user continuously stays in the stopping state, the CPU 10 does not perform any GPS processing as it is (Step S111).

The CPU 10 performs GPS reception start processing only when it is judged that the user changes the moving state by the electric train to a walking state and gets off the electric train (Step S321).

Moreover, in this case, if the user returns from the moving state by the electric train to another moving state by the electric train through a stopping state, the CPU 10 does not start the GPS reception processing also, and sets the electric train boarding flag "OFF.".

On the other hand, when the user moves from the moving state by the electric train to a walking state through a stopping state, the CPU 10 executes walk processing (S121).

In this walk processing, as described above, the CPU 10 starts GPS reception processing at predetermined time intervals to perform the GPS reception processing together with autonomous navigation processing (Steps S221-S224).

When the GPS reception processing ends, the CPU 10 sets the GPS flag and the electric train boarding flag "OFF" (Steps S226 and S227), and calculates the data of the getting-off position by the walk processing (Step S228).

As described above, the positioning apparatus 1 of the modification 1 performs the operation of the GPS reception processing to obtain position data only at the time of boarding and getting-off.

Then, the CPU 10 determines the path through which the movement by the electric train has been performed based on the position data of the two points and the route map data stored in the route map data storage section 13a, and consequently the positioning apparatus 1 can obtain migration path data while suppressing the electric power consumption without performing any GPS receiving operation at all during the running of the electric train.

[Modification 2]

The configuration of the positioning apparatus of a modification 2 is the same as that of the positioning apparatus 1 of the embodiment described above, and the description thereof is omitted.

In the positioning apparatus 1 of the modification 2, when a moving state by an electric train is detected, the positioning apparatus 1 measures the duration time of the moving state by the electric train.

Moreover, the CPU 10 calls the set data of the time interval that has been set in advance to be stored in, for example, the ROM 12.

Then, after the judgment processing of a GPS receiving end state (Step S335), the CPU 10 performs the processing of judging whether the duration time of the moving state by the electric train reaches the set time interval or not.

When the duration time of the moving state by the electric train is equal to or more than the set time interval, the CPU 10 makes the GPS reception processing section 15 perform GPS reception start processing, the processing of setting the GPS flag "ON," and the processing of setting the electric train boarding flag "ON" while the electric train is moving.

Moreover, the CPU 10 resets the duration time of the moving state by the electric train, which duration time the CPU 10 has been measuring.

As described above, the positioning apparatus 1 of the modification 2 can precisely obtain even a path of an electric train that does not stop over a long distance like a super-express electric train while referring to route map data by performing the measurement processing of the present position at suitable time intervals while the electric train is moving.

Moreover, the positioning apparatus 1 of the modification 2 can here omit the present position measurement processing at the time when an electric train stops similarly to the positioning apparatus 1 of the modification 1.

By the omission, the positioning apparatus 1 of the modification 2 comes not to perform the measurement processing of the present position at an unnecessary frequency even if the electric train frequently stops like the case of a local train, an operation at a rush hour, or the like, and consequently the consumption quantity of electric power can be suppressed.

Here, the present invention is not limited to the embodiment described above, and various changes can be performed.

For example, although the aforesaid description of the present invention exemplifies the case where the present invention is applied to the determination of a migration path by an electric train, in which no autonomous navigation can be performed, the present invention can effectively be used for other railroad vehicles, such as a passenger train having no electric power source.

Moreover, although the aforesaid embodiment of the present invention performs the measurement of a position using GPS satellites, the present invention may use other satellite positioning systems, such as GLONASS (Global Navigation Satellite System), or can use position measurement using communications between a cellular phone handset and a base station of the cellular phone.

Moreover, the present invention can also be applied to transportation means having determined routes, such as a trolley bus, other than an electric train by using the judgment of a moving state by a bus with a three-axis acceleration sensor and a three-axis terrestrial magnetism sensor, or an operation input designating the fact that a moving state by an automobile is the movement of public transportation in advance.

Moreover, although the embodiment described above judges the boding and getting-off of a user to an electric train to perform position measurement using GPS satellites, the present invention may especially use the position data nearest to a boarding timing and a getting-off timing without performing the position measurement using the GPS satellites at the time of the boarding and the getting off when the frequency of the position measurement using the GPS satellites is high.

Moreover, although the embodiment described above starts reception processing from a GPS satellite at the timing of the starting of the moving of an electric train, the present invention can also obtain the data of a station where a user has boarded the electric train and the data of a travelling direction from the station where the user has boarded the electric train at the same time by performing the position measurement using the GPS satellite after a predetermined time, for example, 30 seconds, has elapsed after the electric train on which the user has boarded has started a movement.

Moreover, the present invention may improve the identification accuracy of an adjacent station by autonomous navigation or enable the obtainment of the information of a departure platform by performing position measurement using GPS satellites once when an electric train approaches a station to a predetermined distance therefrom, for example, 300 m or less, which approach is detected by, for example, always comparing the station position information of a route map data and position data.

Moreover, although the embodiment described above adopts the mode in which the CPU 10 makes the GPS reception processing section 15, the state judgment processing section 21, and the traveling direction settlement processing section 22 execute each processing based on the program 12*a* stored in the ROM 12, the present invention may be configured to perform all of the pieces of processing by operations of the CPU 10 as software processing.

In addition, the details of the numeral values and the configurations shown in the embodiment can suitably be changed without departing from the spirit and the scope of the present invention.

The entire disclosure of Japanese Patent Application No. 2010-196304 filed on Sep. 2, 2010 including description, claims, drawings, and abstract are incorporated herein by reference in its entirety.

Although various exemplary embodiments have been shown and described, the invention is not limited to the embodiments shown. Therefore, the scope of the invention is intended to be limited solely by the scope of the claims that follow.

The invention claimed is:

1. A positioning apparatus, comprising:
   a position measuring section to obtain measured position data by measuring its own present position;
   a positioning controlling section to control operation timing of the position measuring section to make the position measuring section discontinuously obtain the measured position data;
   a movement measuring section to measure a movement operation;
   a moving method judging section to judge a moving method based on a measurement result of the movement measuring section;
   a map data storage section to store information of a rail route map; and
   a migration path judging section to judge a migration path in a period judged to be a moving state by an electric train by the moving method judging section based on the measured position data measured by the position measuring section and the information of the rail route map.

2. The positioning apparatus according to claim 1, wherein
   the positioning controlling section obtains the measured position data at a first place by making the position measuring section operate when the moving method judging section judges boarding on the electric train, and obtains the measured position data at a second place by making the position measuring section operate when the moving method judging section judges getting-off from the electric train; and
   the migration path judging section determines the migration path in the period of the moving state by the electric train when the measured position data at the first place and the measured position data at the second place are obtained.

3. The positioning apparatus according to claim 2, wherein the positioning controlling section makes the position measuring section operate to obtain the measured position data at a stop place when the moving method judging section judges that the moving method has changed from the moving state by the electric train to a stopping state.

4. The positioning apparatus according to claim 2, wherein the positioning controlling section makes the position measuring section not operate in a period of from obtainment of the measured position data at the first place to judgment of the getting-off from the electric train by the moving method judging section.

5. The positioning apparatus according to claim 1, further comprising:
   a position calculating section to calculate a displacement quantity and a moving direction based on measurement of the movement measuring section, and to calculate the migration path based on the calculated displacement quantity, the calculated moving direction, and position information of a reference in the movement period, wherein
   the position calculating section uses the measured position data as the position information of the reference when the position measuring section obtains the measured position data; and
   the migration path judging section judges the migration path in the period judged to be the moving state by the electric train by the moving method judging section based on the position information obtained by the position measuring section, the position information calculated by the position calculating section, and the information of the rail route map.

6. A positioning method of obtaining a migration path by using a position measuring section to obtain measured position data by measuring a position, a movement measuring section to measure an operation, and information of a rail route map, the method comprising the steps of:
   controlling operation timing of the position measuring section to make the position measuring section discontinuously obtain the measured position data;
   judging a moving method based on a measurement result of the movement measuring section; and
   judging the migration path in a period of an electric train movement judged at the step of judging a moving method based on position information measured by the position measuring section and the information of the rail route map.

7. A storage medium recording a program for a computer to be used for a positioning apparatus, the computer including a position measuring section to obtain measured position data by measuring a position, a movement measuring section to measure an operation, and a map data storage section to store information of a rail route map, the program making the computer function as:
   a positioning controlling section to control operation timing of the position measuring section to make the position measuring section discontinuously obtain the measured position data;
   a moving method judging section to judge a moving method based on a measurement result of the movement measuring section; and
   a migration path judging section to judge a migration path in a period of an electric train movement judged by the moving method judging section based on position information measured by the position measuring section and the information of the rail route map.

* * * * *